United States Patent
Knieriem et al.

(10) Patent No.: US 9,980,481 B2
(45) Date of Patent: May 29, 2018

(54) GRANULES OBTAINABLE BY MILLING PESTICIDE AND SILICA, ADDITION OF ADJUVANT, AND FLUIDIZED BED GRANULATION

(71) Applicant: BASF SE, Ludwigshafen (DE)

(72) Inventors: Torsten Knieriem, Mannheim (DE); Klaus Kolb, Schifferstadt (DE); Payam Michael Miraki Ardestani, Schriesheim (DE)

(73) Assignee: BASF SE, Ludwigshafen (DE)

( * ) Notice: Subject to any disclaimer, the term of this patent is extended or adjusted under 35 U.S.C. 154(b) by 112 days.

(21) Appl. No.: 14/389,970

(22) PCT Filed: Mar. 27, 2013

(86) PCT No.: PCT/EP2013/056471
§ 371 (c)(1),
(2) Date: Oct. 1, 2014

(87) PCT Pub. No.: WO2013/149898
PCT Pub. Date: Oct. 10, 2013

(65) Prior Publication Data
US 2015/0080217 A1    Mar. 19, 2015

Related U.S. Application Data

(60) Provisional application No. 61/618,882, filed on Apr. 2, 2012.

(30) Foreign Application Priority Data

Apr. 2, 2012 (EP) ..................................... 12162879

(51) Int. Cl.
| | | |
|---|---|---|
| *A01N 25/12* | (2006.01) | |
| *A01N 37/38* | (2006.01) | |
| *A01N 37/42* | (2006.01) | |
| *A01N 43/84* | (2006.01) | |

(52) U.S. Cl.
CPC ............. *A01N 25/12* (2013.01); *A01N 37/38* (2013.01); *A01N 37/42* (2013.01); *A01N 43/84* (2013.01)

(58) Field of Classification Search
CPC ......... A01N 25/12; A01N 43/84; A01N 37/42
USPC ....................................................... 504/144
See application file for complete search history.

(56) References Cited

U.S. PATENT DOCUMENTS

| 5,883,047 A | 3/1999 | Jaeger et al. |
| 6,242,382 B1 | 6/2001 | Bratz et al. |
| 2002/0099131 A1 * | 7/2002 | Herbert .................. A01N 25/14 524/547 |
| 2003/0148887 A1 | 8/2003 | Bratz et al. |
| 2004/0062701 A1 * | 4/2004 | Valero .................. C01B 33/193 423/339 |
| 2009/0170704 A1 | 7/2009 | Kober et al. |
| 2015/0018207 A1 | 1/2015 | Knieriem et al. |

FOREIGN PATENT DOCUMENTS

| EP | 0598404 A1 | 5/1994 |
| EP | 1974609 A1 | 10/2008 |
| JP | H08-099802 A | 4/1996 |
| JP | H09-295903 A | 11/1997 |
| JP | 2003-238303 A | 8/2003 |
| WO | WO-9305652 A1 | 4/1993 |
| WO | WO-9955452 A1 | 11/1999 |
| WO | WO-2007/048851 A1 | 5/2007 |
| WO | WO-2007/081553 A2 | 7/2007 |
| WO | WO-2011012495 A1 | 2/2011 |
| WO | WO-2011/054741 A2 | 5/2011 |

OTHER PUBLICATIONS

International Search Report for PCT/EP2013/056471 dated Jun. 7, 2013.
DW2008-M21131/72; Full Translation of previously cited foreign reference EP-1974609-A1 published on Oct. 1, 2008.
DW2011-B35349/13; Full Translation of previously cited foreign reference WO2011/012495-A1 published on Feb. 3, 2011.
International Preliminary Report on Patentability for PCT/EP2013/056471 dated Jul. 10, 2014.

* cited by examiner

*Primary Examiner* — Sreenivasan Padmanabhan
*Assistant Examiner* — Danielle Sullivan
(74) *Attorney, Agent, or Firm* — Drinker Biddle & Reath LLP

(57) ABSTRACT

The present invention relates to a method for preparing granules comprising the steps of A) preparing an adjuvanted slurry by milling an aqueous composition A1 containing a pesticide and a silica absorbent to yield a pesticidal slurry, and adding an adjuvant to the pesticidal slurry; and B) granulating the adjuvanted slurry, wherein the granulation comprises a fluidized bed granulation or sprouted bed granulation. It further relates to granules obtainable be said method comprising 1 to 30 wt % of the pesticide, 10 to 35 wt % of the adjuvant, 8 to 30 wt % of the silica absorbent, and wherein the weight ratio of the silica gel to the adjuvant is from 2/1 to 1/3,5, and finally to a method for controlling phytopathogenic fungi and/or undesired plant growth and/or undesired attack by insects or mites and/or for regulating the growth of plants, where the granules obtainable by said method are allowed to act on the particular pests, their habitat or the plants to be protected from the particular pest, the soil and/or on undesired plants and/or the useful plants and/or their habitat.

19 Claims, No Drawings

GRANULES OBTAINABLE BY MILLING PESTICIDE AND SILICA, ADDITION OF ADJUVANT, AND FLUIDIZED BED GRANULATION

CROSS-REFERENCE TO RELATED APPLICATIONS

This application is a national stage application (under 35 U.S.C. § 371) of PCT/EP2013/056471, filed Mar. 27, 2013, which claims benefit of European Application No, 12162879.6, filed Apr. 2, 2012, and U.S. Application No, 61/618,882, filed Apr. 2, 2012, all of which are incorporated herein by reference in their entirety.

The present invention relates to a method for preparing granules comprising the steps of A) prepaying an adjuvanted slurry by a1) milling an aqueous composition Al containing a pesticide and a silica absorbent to yield a pesticidal slurry, and adding an adjuvant to the pesticidal slurry; or a2) milling an aqueous composition A2 containing a pesticide, a silica absorbent and an adjuvant; and B) granulating the adjuvanted slurry. It further relates to granules obtainable be said method comprising 1 to 30 wt % of the pesticide, 10 to 35 wt % of the adjuvant, 8 to 30 wt % of the silica absorbent, and wherein the weight ratio of the silica gel to the adjuvant is from 2/1 to 1/3,5, and finally to a method for controlling phytopathogenic fungi and/or undesired plant growth and/or undesired attack by insects or mites and/or for regulating the growth of plants, where the granules obtainable by said method are allowed to act on the particular pests, their habitat or the plants to be protected from the particular pest, the soil and/or on undesired plants and/or the useful plants and/or their habitat. Combinations of preferred embodiments with other preferred embodiments are within the scope of the present invention.

Usually it is difficult to include adjuvants, especially liquid adjuvants into granular agrochemical formulations.

EP 1 974 609 discloses a method for preparing granules by (1) forming an absorbate by mixing an adjuvant and an silica absorbent, (2) forming an aqueous suspension by wet milling, (3) addition of the absorbate to the aqueous suspension, and (4) granulation. This method has disadvantages, such as the requirement to prepare in a separate, additional step an absorbate of the adjuvant to silica.

U.S. Pat. No. 6242382B1 discloses in Example 1 the mixing and grounding of a pesticide, Wettol® LF700 and Extrusil®, followed by fluidized bed granulation. This method has disadvantages, such as the chemical destruction of sensitive additives, such as Wettol® L.F700 during the grounding.

Object of the present invention was to overcome these afore mentioned problems. Another object of the present invention was to avoid an additional step of absorption of the adjuvant to solid carriers prior to milling. Another object of the present invention was to avoid the milling of sensitive additives, such as the adjuvant.

The object was solved by a method for preparing granules comprising the steps of A) preparing an adjuvanted slurry by milling an aqueous composition Al containing a pesticide and a silica absorbent to yield a pesticidal slurry, and adding an adjuvant in liquid form to the pesticidal slurry; and B) granulating the adjuvanted slurry, wherein the granulation comprises a fluidized bed granulation or sprouted bed granulation.

Suitable adjuvants are compounds, which have a negligible or even no pesticidal activity themselves, and which improve the biological performance of the pesticide on the target, Further examples are listed by Knowles, Adjuvants and additives, Agrow Reports DS256, T&F Informa UK, 2006, chapter 5.

The adjuvant is preferably a liquid at 20° C. and 1013 mbar. The freezing point of the adjuvant may be below 20° C., preferably below 10° C. The adjuvant may be water-insoluble or water-soluble, wherein the latter is preferred.

In step A) (this means at the point of time when step A) is carried out) the adjuvant is added in liquid form to the pesticidal slurry. The adjuvant in step A) is preferably free of solids, such as solid carriers or solid absorbers. The adjuvant in step A) usually contains less than 5 wt %, preferably less than 2 wt %, and in particular less than 0.5 wt % solids.

Typically, the adjuvant, which is added in step A) in liquid form to the pesticidal slurry, is present in highly concentrated form, Preferably, the adjuvant which is added in step A) in liquid form to the pesticidal slurry, is has a purity of at least 50 wt %, more preferably at least 70 wt %, and in particular at least 90 wt %. Preferably, the adjuvant which is added in step A) in liquid form to the pesticidal slurry, contains less than 50 wt %, more preferably less than 30 wt %, and in particular less than 10 wt % of other compounds.

Typically, step A) is carried out at temperatures between 5 and 200° C. Preferably, step A) is carried out at temperatures between 5 and 70° C., more preferably between 10 and 50° C., and in particular between 10 and 35° C.

The adjuvant is preferably an alkoxylate, more preferably a liquid alkoxylate. Examples of alkoxylates are compounds such as alkanol alkoxylates, alkylphenol polyglycol ethers, ethoxylated sorbitan fatty acid esters, alkylpolyglucosides, fatty acid glucamides, fatty acid polyglycol esters, fatty alcohols, fatty amine alkoxylates, fatty acid amide alkoxylates, polyglycerol fatty acid esters, fatty acid alkanolamides, polyether modified siloxanes, or ethylene oxide/propylene oxide block polymers.

Preferred adjuvants are alkanol alkoxylates (preferably a liquid alkanol alkoxylate), such as those of the formula (I))

$$R^a\text{—O-(AO)}_m\text{—}R^1 \qquad \text{formula (I)}$$

in which $R^a$ is straight-chain or branched alkyl or alkylene with from 4 to 32, preferably from 10 to 22, carbon atoms, AO is an ethylene oxide radical, propylene oxide radical, butylene oxide radical, pentylene oxide radical, styrene oxide radical or mixtures of the abovernentioned radicals in random or block sequence, m is numbers from 1 to 30 and $R^1$ is hydrogen or alkyl with from 1 to 4 carbon atoms.

Particularly preferred alkanol alkoxylates are those of the formula (II)

$$R^b\text{—O-(EO)}_p\text{—(PO)}_q\text{—}R^1 \qquad \text{formula (II)}$$

in which $R^b$ is straight-chain or branched alkyl or alkylene with from 4 to 32, preferably from 10 to 22, particularly preferably from 6 to 18, carbon atoms, EO is —$CH_2CH_2$—O—, PO is —$CH_2$—$CH(CH_3)$—O— or —$(CH_2)_3$—O—, p is numbers from 0 to 20, preferably from 3 to 10, in particular from 4 to 8, q is numbers from 1 to 25, preferably from 4 to 15, and $R^1$ is hydrogen or alkyl with from 1 to 4 carbon atoms, in which the EO and PO units can occur in random sequence or as blocks.

In an additional embodiment, with the alkanol alkoxylate of the formula (II), $R^b$ is straight-chain or branched alkyl or alkylene with from 4 to 32, preferably from 6 to 22, particularly preferably from 10 to 18, carbon atoms, q is numbers from 1 to 25, preferably from 3 to 15, and the other radicals as described above for the formula (II).

An additional particularly preferred embodiment are alkanol alkoxylates of the formula (III)

$$R^c\!-\!\!O\!-\!(EO)_p\text{-}(BO)_q\!-\!R^1 \qquad \text{formula (III)}$$

in which $R^c$ is straight-chain or branched alkyl or alkylene with from 4 to 32, preferably from 7 to 18, carbon atoms.

EO is $-CH_2CH_2-O-$,

BO is $-C_4H_8O-$, which can be linear or branched, p is numbers from 1 to 25, preferably from 3 to 12, in particular from 4 to 7, q is numbers from 1 to 25, preferably from 1 to 15, in particular from 1 to 7, and $R^1$ is hydrogen or alkyl with from 1 to 4 carbon atoms, in which the EO and BO units can occur in random sequence or as blocks.

An additional particularly preferred embodiment are alkanol alkoxylates of the formula (IV)

$$R^d\!-\!\!O\text{ -}(EO)_p\!-\!R^1 \qquad \text{formula (IV)}$$

in which $R^d$ is straight-chain or branched alkyl or alkylene with from 4 to 32, preferably from 10 to 15, carbon atoms, EO is $-CH_2CH_2-O-$, p is numbers from 1 to 10, preferably from 1 to 3, $R^1$ is hydrogen or alkyl with from 1 to 4 carbon atoms.

Suitable silica absorbents are usually based on precipitated silicas, aluminium and/or calcium silicates, and are commercially available as Sipemat® from Evonik Industries, Germany. The silica absorbent is usually present as fine particle silica, such as in form of a powder.

The silica absorbent may have a particle size distribution (determined by laser diffraction, ISO 13320-1) $D_{50}$ of less than 60 µm, preferably of $D_{50}$ of less than 15 µm, and in particular of $D_{50}$ of less than 10 µm. In another form the siiica absorbent may have a particle size distribution (determined by diffraction, ISO 13320-1) $D_{50}$ of less than 60 µm and $D_{90}$ of less than 150 µm, preferably of $D_{50}$ of less than 15 µm and $D_{90}$ of less than 25 µm, and in particular of $D_{50}$ of less than 10 µm and $D_{90}$ of less than 18 µm. The particle size distribution relates to the silica absorbent before it is subjected to the milling in step A).

The silica absorbent may have a specific surface area (determined by an Areameter with nitrogen, ISO 5794-1, Annex D) of less than 200 m$^2$/g, preferably less than 150 m$^2$/g, and in particular less than 100 m$^2$g. The surface area relates to the silica absorbent before it is subjected to the milling in step A).

The silica absorbent may have a absorbent capacity from 600 to 160 g, preferably from 300 to 170 g, and in particular from 250 to 180 g DBP per 100 g solid carrier (determined by DIN 53601).

The steps A) and B) are usually made in the given sequence. The adjuvanted slurry may have a solid content of 10 to 70 wt %, preferably from 20 to 60 wt %.

The milling of the aqueous composition A1 may be done by conventional milling processes, such as wet-milling (e.g. by beads mill). The milling may be continued until the desired particle size distribution of the adjuvanted slurry is obtained. Usually, the particle size distribution $D_{50}$ of the adjuvanted slurry is from 0,2 to 20 µm, preferably from 0,5 to 5 µm. The granulation of step B) comprises a fluidized bed granulation or sprouted bed granulation, wherein the fluidized bed granulation is more preferred. The fluidized bed granulation is well known, such as from U.S. Pat. No. 5,883,047.

The adjuvanted slurry may be subjected to fluidized-bed granulation, the adjuvanted slurry being sprayed onto the fluidized bed against the direction of flow of the heated fluidized gas.

The inlet temperature of the fluidized gas is usually from 50 to 220° C., in particular from 70 to 200° C.

The amount of fluidized gas is usually from 10 to 500 and in particular from 50 to 300 m$^3$/min per m$^2$ of incident flow area of the fluidized bed.

The spray rate and the concentration of the product in the aqueous solution or dispersion must in this case always be adapted to the particular conditions, The suitable values can be determined by means of a few routine tests.

For spraying with nozzle of the adjuvanted slurry, one or more two-substance nozzles or three-substance nozzles are preferably used, which are operated using an inert gas, in general compressed air, at from 1.2 to 5.0 bar. The temperature of the compressed air is in general in the range from 15 to 100° C.

The process according to the invention can be carried out continuously or batchwise.

The residual moisture of the granules obtained is preferably less than or equal to 4 percent by weight, in particular less than or equal to 2 percent by weight and particularly preferably less than or equal to 1 percent by weight.

The granules may have a particle size distribution of D 50 from 0,05 to 10 mm, preferably from 0,1 to 5 mm. The granules may have a particle size distribution of D90 from 0,1 to 15 mm, preferably from 0,3 to 7 mm.

The granules may contain an anionic dispersant. The anionic dispersant may be solid at 20 Suitable anionic dispersants are akali, alkaline earth or ammonium salts of sulfonates, sulfates, phosphates, carboxylates, and mixtures thereof. Examples of sullonates are alkylaryl-sulfonates, diphenylsulfonates, alpha-olefin sulfonates, lignine sulfonates, sulfonates of fatty acids and oils, sultanates of ethoxylated alkylphenols, sulfonates of alkoxylated arylphenols, sulfonates of condensed naphthalenes, sultanates of dodecyl- and tridecylbenzenes, sultanates of naphthalenes and alkylnaphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters, Examples of carboxylates are alkyl carboxylates, carboxylated alcohol or alkylphenol ethoxylates, and alkali salts of polyacrylic acid, polyacrylic acid copolymers, or polyacid comb polymers. Preferred anionic dispersants are sulfonates and carboxylates.

The granules may comprise auxiliaries. Examples for suitable auxiliaries are solvents, liquid carriers, solid carriers, surfactants, emulsifiers, wetters, solubilizers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are organic solvents, such as mineral oil fractions of medium to high boiling point, e.g. kerosene, diesel oil; oils of vegetable or animal origin; aliphatic, cyclic and aromatic hydrocarbons, e.g. toluene, paraffin, tetrahydronaphtalene, alkylated naphthalenes; alcohols, e.g. ethanol, propanol, butanol, benzylalcohol, cyclohexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof. Usually, the granules are essentially free of organic solvents, e.g. they comprise less than 5 wt %, preferably less than 2 wt %, and in particular less than 0,2 wt % organic solvent.

Suitable solid carders are mineral earths, e.g. talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof. The silica absorbent is not considered a solid carrier within the meaning of this invention. Solid carriers preferably have a low absorbent capacity, such as less than 160 g (preferably less than 130 g) DBP per 100 g solid carrier (determined by DIN 53601). The granules may contain less than 30 wt %, preferably less than 20 wt %, and in particular less than 12 wt % of the solid carrier (e.g. the solid carrier having a low absorbing capacity).

Suitable surfactants are surface-active compounds, such as cationic, nonionic and amphoteric surfactants, block polymers, polyelectrolytes, and mixtures thereof. Such surfactants can be used as emusifier, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed, or North American Ed.). The granules may contain the adjuvant, which also act as surfactants. In case a surfactant is within the scope of the claim definition of the adjuvant, it is not considered as a surfactant within the meaning of this invention.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents, Ethylene oxide and/or propylene oxide may be employed for the alkoxylation, preferably ethylene oxide. Examples of N-subsititued fatty acid amides are fatty acid glucamides or fatty acid alkanolarnides, Examples of esters are fatty acid esters, glycerol esters or monoolycerides. Examples of sugar-based surfactants are sorbitans, ethoxylated sorbitans, sucrose and glucose esters or alkylpolyglucosides. Examples of polymeric surfactants are home- or copolymers of vinylpyrrolidone, vinyialcohols, or vinylacetate, Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B-C type comprising alkanol, polyethylene oxide and polypropylene oxide.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

The term pesticide refers to at least one active substance selected from the group of the fungicides, insecticides, nematicides, herbicides, safeners and/or growth regulators. Preferred pesticides are fungicides, insecticides, herbicides and growth regulators. Especially preferred pesticides are fungicides. Mixtures of pesticides of two or more of the abovementioned classes may also be used. The skilled worker is familiar with such pesticides, which can be found, for example, in the Pesticide Manual, 15th Ed. (2009), The British Crop Protection Council, London. Suitable insecticides are insecticides from the class of the carbamates, organophosphates, organochlorine insecticides, phenylpyrazoles, pyrethroids, neonicotinoids, spinosins, avermectins, milbernycins, juvenile hormone analogs, alkyl halides, organotin compounds nereistoxin analogs, benzoylureas, diacylhydrazines, METI acarizides, and insecticides such as chloropicrin, pymetrozin, flonicamid, ciofentezin, hexythiazox, etoxazole, diafenthiuron, propargite, tetradifon, chlorofenapyr, DNOC, buprofezine, cyrornazine, amitraz, hydramethylnon, acequinocyl, fluacrypyrim, retenone, or their derivatives.

Suitable fungicides are fungicides from the classes of dinitroanilines, allylamines, anilinopyrimidines, antibiotics, aromatic hydrocarbons, benzenesulfonarnides, benzimidazoles, benzisothiazoles, benzophenones, benzothiadiazoles, benzotriazines, benzyl carbamates, carbamates, carboxamides, carboxylic acid diamides, chloronitriles cyanoacetamide oximes, cyanoimidazoles, cyclopropanecarboxamides, dicarboximides, dihydrodioxazines, dinitrophenyl crotonates, dithiocarbamates, dithiolanes, ethylphosphonates, ethylaminothiazolecarboxamides, guanidines, hydroxy-(2-amino)pyrimidines, hydroxyanilides, imidazoles, imidazolinones, inorganic substances, isobenzofuranones, methoxyacrylates, methoxycarbamates, morpholines, N-phenylcarbarnates, oxazolidinediones, oximinoacetates, oximinoacetamides, peptidylpyrimidine nucleosides, phenylacetamides, phenylamides, phenylpyrroles, phenylureas, phosphonates, phosphorothiolates, phthalamic acids, phthalimides, piperazines, piperidines, propionamides, pyridazinones, pyridines, pyridinylmethylbenzamides, pyrimidinamines, pyrimidines, pyrimidinonehydrazones, pyrroloquinolinones, quinazolinones, quinolines, quinones, sulfamides, sulfamoyltriazoles, thiazolecarboxamides, thiocarbamates, thiophanates, thiophenecarboxamides, toluamides, triphenyltin compounds, triazines, triazoles. Suitable herbicides are herbicides from the classes of the acetamides, amides, aryloxyphenoxypropionates, benzamides, benzofuran, benzoic acids, benzothiadiazinones, bipyridylium, carbamates, chloroacetamides, chlorocarboxylic acids, cyclohexanediones, dinitroanilines, dinitrophenol, diphenyl ether, glycines, imidazolinones, isoxazoles, isoxazolidinones, nitriles, N-phenylphthalimides, oxadiazoles, oxazolidinediones, oxyacetamides, phenoxycarboxylic acids, phenylcarbamates, phenylpyrazoles, phenylpyrazolines, phenylpyridazines, phosphinic acids, phosphoroamidates, phosphorodithioates, phthalamates, pyrazoles, pyridazinones, pyridines, cyridinecarboxylic acids, pyridinecarboxamides, pyrimidinediones, pyrimidinyl(thio)benzoates, quinolinecarboxylic acids, semicarbazones, sulfonylaminocarbonyitriazolinones, sulfonylureas, tetrazolinones, thiadiazoles, thiocarbamates, triazines, triazinones, triazoles, triazolinones, triazolocarboxamides, triazolopyrimidines, triketones, uracils, ureas.

In another form the pesticide may be N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; N-[4-chloro-2-[(diethyl-lambda-4-sulfanylidene)carbamoyl]-6-methyl-phenyl]-2-(3-chloro-2-pyridyl)-5-(trifluoromethyl)pyrazole-3-carboxamide; N-[4-chloro-2-[(di-2-propyl-lambda-4-sulfanylidene)carbamoyl]-6-methyl-phenyl]-2-(3-chloro-2-pyridyl)-5-(trifluoromethyppyrazole-3-carboxamide; N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-dichloro-2-[(diethyl-lambda-4-sulfanylidene)carbamoyl]-phenyl]-2-(3-chloro-2-pyridyl)-5-(difluoromethyl)pyrazole-3-carboxamide; N-[4,6-dibromo-2-[(di-2-propyl-lambda-4-sulfanylidene)carbamoyl]-phenyl]-2-(3-chloro-2-pyridyl)-5-(trifluoromethyl)pyrazole-3-carboxamide; N-[4,6-chloro-2-[(di-2-propyl-lambda-4-sulfanylidene)carbamoyl]-6-cyanophenyl]-2-(3-chloro-2-pyridyl)-5-(trifluorornethyl)pyrazole-3-carboxamide: or N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide.

The pesticide has preferably a melting point of at least 30° C., and in particular a least 50° c.

The pesticide is preferably water-insoluble. Usually, the pesticide has solubility in water at 20° C. of up to 10 g/l, preferably up to 1 g/l, and in particular up to 0,2 gl.

The granules may contain from 0,1 to 50 wt %, preferably from 5 to 35 wt %, and in particular from 10 to 25 wt % of the pesticide.

The granules may contain at least 10 wt %, preferably at least 13 wt %, and in particular at least 17 wt % of the adjuvant. The granules may contain up to 40 wt %, preferably up to 35 wt %, and in particular up to 30 wt % of the adjuvant.

The granules may contain at least 4 wt %, preferably at least 8 wt %, and in particular at least 10 wt % of the silica absorbent. The granules may contain up to 45 wt %, preferably up to 35 wt %, and in particular up to 25 wt % of the silica absorbent.

The weight ratio of the silica gel to the adjuvant may be from 2/1 to 1/3,5, preferably from 1,5/1 to 1/2,5, and in particular from 1,1/1 to 1/1,9.

The granules may contain at least 3 wt %, preferably at least 6 wt %, and in particular at least 10 wt % of the anionic dispersant. The granules may contain up to 60 wt %, preferably up to 50 wt %, and in particular up to 40 wt % of the anionic dispersant.

The granules may contain 5-35 wt % of the pesticide, 13-35 wt % of the adjuvant, 8-35 wt % of the silica absorbent, and optionally 6-50 wt % of the dispersant. The granules may preferably contain 10-25 wt % of the pesticide, 17-30 wt % of the adjuvant, 10-25 wt % of the silica absorbent, and optionally 10-40 wt % of the dispersant.

Usually, the sum of all components present in the granules adds up to 100%.

The present invention also relates to granules obtainable by (preferably obtained by) the method according to the invention and comprising
1 to 30 wt % of the pesticide,
10 to 35 wt % of the adjuvant,
8 to 30 wt % of the silica absorbent,
optionally filled up to 100 wt % with anionic dispersant,
and wherein the weight ratio of the silica gel to the adjuvant is from 2/1 to 1/3,5.

Preferably, the granules are obtainable by the method according to the invention and comprising 5-35 wt % of the pesticide, 13-35 wt % of the adjuvant, 8-35 wt % of the silica absorbent, (and optionally 6-50 wt % of the dispersant), and wherein the weight ratio of the silica gel to the adjuvant is from 2/1 to 1/3,5.

More preferably, the granules are obtainable by the method according to the invention and comprising 10-25 wt % of the pesticide, 17-30 wt % of the adjuvant, 10-25 wt % of the silica absorbent, (and optionally 10-40 wt % of the dispersant), and wherein the weight ratio of the silica gel to the adjuvant is from 1,5/1 to 1/2,5.

The present invention also relates to a method for controlling phytopathogenic fungi and/or undesired plant growth and/or undesired attack by insects or mites and/or for regulating the growth of plants, where the granules obtainable by the method according to the invention are allowed to act on the particular pests, their habitat or the plants to be protected from the particular pest, the soil and/or on undesired plants and/or the useful plants and/or their habitat.

When employed in plant protection, the amounts of active substances applied are, depending on the kind of effect desired, from 0.001 to 2 kg per ha, preferably from 0.005 to 2 kg per ha, more preferably from 0.05 to 0.9 kg per ha, in particular from 0.1 to 0.75 kg per ha.

The user applies the composition according to the invention in form of a ready-to-use spray liquor usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor is thus obtained. Usually, 20 to 2000 liters, preferably 50 to 400 liters, of the ready-to-use spray liquor are applied per hectare of agricultural useful area.

The present invention offers various advantages: Various silica absorbents may be applied in the method, even those with a low surface area, or with a high partice size, or with a low absorption capacity; the granules may contain a high concentration of the adjuvant, especially of the liquid adjuvant; the granules are storage stable, e.g. even at elevated temperatures up to 54° C.; the granules show no caking upon storage; there is no loss of the adjuvant during the preparation of the granules; the granules disperse easily upon dispersion in water and they form a stable dispersion. Further on, there is no time-consuming and costly requirement to prepare in a separate, additional step an absorbate of the adjuvant to silica. Further on, milling of the aqueous composition results in smaller particles (compared to milling without water) in the pesticidal slurry, which is important to allow for a fluidized bed or sprouted bed granulation. Further on, the present invention avoids an additional step of absorption of the adjuvant to solid carriers prior to milling; and the present invention avoids the milling of sensitive additives, such as the adjuvant.

EXAMPLES

Silica A: Precipitated silica powder, average particle size 3 µm, particle size D50 4,5 µm, DBP absorption 210 g/100 g, specific surface (nitrogen) 50 m²/g.

Carrier A: Natural kaolinic clay powder, density 2,6, insoluble in water.

Adjuvant A: liquid, nonionic ethoxylated and propoxylated C12-18 alcohol, freezing point −7° C., insoluble in water, dynamic viscosity at 23° C. about 110-125 mPas.

Adjuvant B: liquid, nonionic ethoxylated and propoxylated C12-18 alcohol, freezing point −5° C., insoluble in water, dynamic viscosity at 23° C. about 95-110 mPas.

Adjuvant liquid, nonionic alkoxylated fatty alcohol, insoluble in water, dynamic viscosity at 23° C. about 70-80 mPas.

Adjuvant C: liquid, nonionic alkoxylated fatty alcohol.

Adjuvant E: liquid, nonionic alkoxylated fatty alcohol, soluble in water, dynamic viscosity at 23° C. about 80-90 mPas.

Adjuvant F: liquid, water-soluble polyether modified trisiloxane, viscosity at 25° C. about 50-80 mPas, pour point below −10° C.

Adjuvant G: Liquid, water-soluble fatty alcohol alkoxyiate phophoric acid ester, acid value 200-220 mgKOH/g, water content about 13%, freezing point −4° C.

Adjuvant H: liquid, nonionic ethoxylated and propoxylated C12-18 alcohol, dynamic viscosity at 20° C. about 90-105 mPas.

Antifoarn A: Silfoam® SRE, an aqueous, nonionic silicone emulsion, solid content 33%.

Disperant A: Polyalkyl napphtalene sulphonate powder, water soluble.

Dispersant B: Sodium dodecyl sulfate,

Dispersant C: Naphthalenesulfonic acid-fomaldehyde-polycondensate, sodium salt, water-soluble poweder.

Dispersant D: Sodium lighosulphonate, water-soluble powder.

Dispersant E: Sodium lignin sulfonate, water-soluble powder.

Dispersant Sodium polycarboxylate (polymer of 2,5-furandione with 2,4,4-trimethylpentene, sodium salt), water-soluble powder.

Example 1

An aqueous suspension was prepared by chilling a composition containing the pesticide dimethomorph, the silica absorbent Silica A, and optionally further additives in a ball mill (cf Tables 1 and 2), The resulting particle size of the pesticide was D50<2 μm.

The liquid adjuvant and the Antifoarn A were added to the aqueous suspension (i.e. the aqueous slurry of step A) according to the invention).

Finally, granules were prepared by injection the adjuvanted suspension (solid content 40 wt %) into a fluidized bed granulation device (product temperature 55° C.). The water content was below 2 wt %. The granules had a particle size distribution of about D50=0,6 mm and D90=1,0 mm. The composition of the resulting granules, which contained each 20 wt % dimethomorph, 2 wt % Anti-foam A, and Dispersant A ad 100 wt %, is summarized in Table 1 and 2. The composition of the resulting granules, which contained each 20 wt % dimethomorph and 2 wt % Antifoam A, is summarized in Table 3, The amount of adjuvant in the granules was analyzed and confirmed by HPLC, thus no adjuvant was evaporated during granulation.

TABLE 1

Composition of granules (wt %)

|  | A | B | C |
|---|---|---|---|
| Silica A | 15 | 25 | 17.5 |
| Adjuvant A | 25 | 30 | 30 |
| Dispersant B | 1.5 | 1.5 | 1.5 |

TABLE 2

Composition of granules (wt %)

|  | D | E | F | G | H | I | J | K |
|---|---|---|---|---|---|---|---|---|
| Silica A | 12.5 | 19 | 16 | 16 | 16 | 16 | 16 | 16 |
| Adjuvant B | 20 | 30 |  |  |  |  |  |  |
| Adjuvant C |  |  | 25 |  |  |  |  |  |
| Adjuvant D |  |  |  | 25 |  |  |  |  |
| Adjuvant E |  |  |  |  | 25 |  |  |  |
| Adjuvant F |  |  |  |  |  | 25 |  |  |
| Adjuvant G |  |  |  |  |  |  | 25 |  |
| Adjuvant H |  |  |  |  |  |  |  | 25 |
| Dispersant B | 1.5 | 1.5 | 1.5 | 1.5 | 1.5 | 1.5 | 1.5 | 1.5 |
| Carrier A | 10 |  |  |  |  |  |  |  |

TABLE 3

Composition of granules (wt %)

|  | M | N | O | P | Q | R |
|---|---|---|---|---|---|---|
| Silica A | 12.5 | 12.5 | 12.5 | 16 | 16 | 16 |
| Adjuvant A | 20 | 20 | 20 | 15 | 15 | 15 |
| Adjuvant C |  |  | 10 |  |  |  |
| Adjuvant D |  |  |  | 10 |  |  |
| Adjuvant E |  |  |  |  |  | 10 |
| Carrier A | 10 | 10 | 10 |  |  |  |
| Dispersant B | 1.5 | 1.5 | 1.5 | 1.5 | 1.5 | 1.5 |
| Dispersant C | 12 |  |  |  |  |  |
| Dispersant D | Ad 100 |  |  |  |  |  |
| Dispersant E |  | Ad 100 |  |  |  |  |
| Dispersant F |  |  | Ad 100 |  |  |  |
| Dispersant A |  |  |  | Ad 100 | Ad 100 | Ad 100 |

Example 2

An aqueous suspension was prepared by milling a composition containing prohexadione-calcium, trinexapac-ethyl, the silica absorbent Silica A, and further additives in a bail mill (see below). The resulting particle size of the pesticide was D50<2 μm.

The liquid adjuvant and the Antifoam A were added to the aqueous suspension. Finally, granules were prepared by injection the adjuvanted suspension into a fluidized bed granulation device as described in Example 1.

The final granules contained 5% prohexadion-calcium, 7,5% trinexapac ethyl, 1% Antifoam A, 15% Silica A. 10% lignosulfonic acid sodium salt, 5% nonionic surfactant, 7,5% Adjuvant A. 7,5% Adjuvant D, 2% water and ammonium sulphate up to 100 wt %. The granules had a particle size distribution of about D50=0,6 mm and D90=1,0 mm.

Example 3

The storage stability of the granules prepared in Examples 1A, D, I, J and P was tested after two weeks storage at 54° C. according to CIPAC MT 46.1.1 (Table 4-6). Caking was tested while storing under a pressure of 25 g/cm². The particle size distribution was determined by a Malvern Master-sizer after dilution with water ($D_{50}$ and $D_{90}$ presented as 1'/US). To determine the dispersion stability a 2% dilution in a 100 ml graduated cone shaped cylinder was prepared. The volume of the sediment was checked after 2 h storage. The pH value was determined at a concentration of 1 wt % in water at 20

TABLE 4

Storage stability after 2 weeks at 54° C.

| | Sample | | | |
|---|---|---|---|---|
| | 1A Initial | 1A Stored | 1D Initial | 1D Stored |
| Caking | No | No | No | No |
| pH | 8.2 | 8.4 | 8.5 | 8.6 |
| Particle size | $D_{50}$: 1.8/ 1.3 μm $D_{90}$: 18.9/ 5.8 μm | $D_{50}$: 4.5/ 1.7 μm $D_{90}$: 29.6/ 11.4 μm | $D_{50}$: 1.5/ 1.4 μm $D_{90}$: 5.7/ 4.8 μm | $D_{50}$: 1.8/ 1.4 μm $D_{90}$: 8.2/ 5.5 μm |
| Dispersion stability | 0.25 ml No creaming | 0.65 ml No creaming | <0.1 ml No creaming | 0.1 ml No creaming |

TABLE 5

Storage stability after 2 weeks at 54° C.

| | Sample | | | |
|---|---|---|---|---|
| | 1I Initial | 1I Stored | 1J Initial | 1J Stored |
| Caking | No | No | No | No |
| pH | 8.5 | 8.5 | 2.5 | 2.5 |
| Particle size | $D_{50}$: 1.3/ 1.2 μm $D_{90}$: 3.8/ 4.0 μm | $D_{50}$: 1.3/ 1.5 μm $D_{90}$: 6.3/ 6.0 μm | $D_{50}$: 1.3/ 1.3 μm $D_{90}$: 5.0/ 5.4 μm | $D_{50}$: 1.5/ 1.6 μm $D_{90}$: 6.8/ 6.7 μm |
| Dispersion stability | <0.05 ml No creaming | <0.05 ml No creaming | <0.05 ml No creaming | <0.05 ml No creaming |

TABLE 6

Storage stability after 2 weeks at 54° C.

| | Sample | |
|---|---|---|
| | 1P Initial | 1P Stored |
| Caking | No | No |
| pH | 8.2 | 8.1 |
| Particle size | $D_{50}$: 2.2/1.6 μm $D_{90}$: 6.8/4.9 μm | $D_{50}$: 2.4/1.8 μm $D_{90}$: 6.9/5.3 μm |
| Dispersion stability | <0.05 ml No creaming | 0.05 ml No creaming |

We claim:

1. A method for preparing granules comprising the steps of:
    A) preparing an adjuvanted slurry by milling an aqueous composition containing a pesticide and a silica absorbent to yield a pesticidal slurry, wherein the milling of the aqueous composition is continued till the particle size distribution $D_{50}$ of the adjuvanted slurry is from 0.2 to 20 μm, and adding an adjuvant in liquid form to the pesticidal slurry after milling, and
    B) granulating the adjuvanted slurry, wherein the granulation comprises a fluidized bed granulation or sprouted bed granulation;
    wherein the adjuvant is one or more alkoxylates,
    wherein the granules comprise:
    10 to 25 wt% of the pesticide,
    17 to 30 wt% of the adjuvant, and
    10 to 25 wt% of the silica absorbent,
    and wherein the weight ratio of the silica absorbent to the adjuvant is from 1.5/1 to 1/2.5.

2. The method according to claim 1, wherein the alkoxylate is an alkanol alkoxylate, an alkylphenol polyglycol ether, an ethoxylated sorbitan fatty acid ester, an alkylpolyglucoside, a fatty acid glucamide, a fatty acid polyglycol ester, a fatty alcohol, a fatty amine alkoxylate, a fatty acid amide alkoxylate, a polyglycerol fatty acid ester, a fatty acid alkanolamide, a polyether modified siloxane, or an ethylene oxide/propylene oxide block polymer.

3. The method according to claim 1, wherein the adjuvant is a liquid at 20° C.

4. The method according to claim 1, wherein the adjuvant is an alkanol alkoxylate of the formula (I)

$$R^a\text{—}O\text{—}(AO)_m\text{—}R^1 \quad (I)$$

in which
    $R^a$ is straight-chain or branched alkyl or alkylene with from 4 to 32 carbon atoms,
    AO is an ethylene oxide radical, propylene oxide radical, butylene oxide radical, pentylene oxide radical, styrene oxide radical or a mixture of the ethylene oxide radical, the propylene oxide radical, the butylene oxide radical, the pentylene oxide radical, and the styrene oxide radical in random or block sequence,
    m is a number from 1 to 30, and
    $R^1$ is hydrogen or alkyl with from 1 to 4 carbon atoms.

5. The method according to claim 4, wherein $R^a$ is straight-chain or branched alkyl or alkylene with from 10 to 22 carbon atoms.

6. The method according to claim 1, wherein the adjuvant in step A) contains less than 5 wt % solids.

7. The method according to claim 1, wherein the pesticide has a melting point of at least 30 ° C.

8. The method according to claim 1, wherein the silica absorbent has a particle size distribution $D_{50}$ of less than 15 μm and $D_{90}$ less than 25 μm.

9. The method according to claim 1, wherein the silica absorbent has a specific surface area of less than 200 $m^2$/g.

10. The method according to claim 1, wherein the granules contain at least 10 wt % of an anionic dispersant.

11. The method according to claim 1, wherein the granules contain less than 12 wt % of a solid carrier with low absorbing capacity.

12. The method according to claim 1, wherein the granules are essentially free of organic solvents.

13. Granules obtained by the method of claim 1.

14. A method for controlling phytopathogenic fungi and/or undesired plant growth and/or undesired attack by insects or mites and/or for regulating the growth of plants, where the granules obtainable by the method of claim 1 are allowed to act on the particular pests, their habitat or the plants to be protected from the particular pest, the soil and/or on undesired plants and/or the useful plants and/or their habitat.

15. The method according to claim 1, wherein the granules further comprise one or more auxiliaries.

16. The method according to claim 1, wherein the pesticide comprises at least one active substance selected from the group consisting of fungicides, insecticides, nematicides, herbicides, safeners, and/or growth regulators.

17. The granules according to claim 13, wherein the granules comprise one or more auxiliaries.

18. The granules according to claim 13, wherein the pesticide comprises at least one active substance selected from the group consisting of fungicides, insecticides, nematicides, herbicides, safeners, and/or growth regulators.

19. The method of claim 1, wherein the milling of the aqueous composition is continued till the particle size distribution $D_{50}$ of the adjuvanted slurry is from 0.5 to 5μm.

* * * * *